(12) United States Patent
Tan

(10) Patent No.: US 7,454,988 B2
(45) Date of Patent: Nov. 25, 2008

(54) METHOD FOR FLUID SAMPLING USING ELECTRICALLY CONTROLLED DROPLETS

(75) Inventor: Roy H. Tan, Union City, CA (US)

(73) Assignee: Applera Corporation, Foster City, CA (US)

( * ) Notice: Subject to any disclaimer, the term of this patent is extended or adjusted under 35 U.S.C. 154(b) by 268 days.

(21) Appl. No.: 11/351,706

(22) Filed: Feb. 9, 2006

(65) Prior Publication Data

US 2006/0186048 A1    Aug. 24, 2006

Related U.S. Application Data

(60) Provisional application No. 60/680,914, filed on May 13, 2005, provisional application No. 60/651,865, filed on Feb. 10, 2005.

(51) Int. Cl.
*G01N 1/10* (2006.01)
*G01N 1/22* (2006.01)
*G01N 1/40* (2006.01)

(52) U.S. Cl. .................. 73/863.21; 73/28.04; 73/28.05; 73/864.81; 204/600; 422/83; 422/88

(58) Field of Classification Search ............... 73/23.22, 73/23.3, 23.34, 23.35, 28.01, 28.04–28.06, 73/31.01–31.03, 31.07, 863.21, 863.22, 863.23, 73/863.24, 863.41, 864.81, 864.71; 204/600, 204/643, 648; 422/83, 84, 88, 89, 94
See application file for complete search history.

(56) References Cited

U.S. PATENT DOCUMENTS

| | | | |
|---|---|---|---|
| 4,363,639 A * | 12/1982 | Gladon | ........................ 95/226 |
| 4,565,086 A | 1/1986 | Orr, Jr. | |
| 5,571,410 A | 11/1996 | Swedberg et al. | |
| 5,656,196 A | 8/1997 | Tasuda et al. | |
| 5,667,716 A | 9/1997 | Ziolo et al. | |
| 5,851,416 A | 12/1998 | Raj et al. | |
| 5,879,580 A | 3/1999 | Tasuda et al. | |
| 5,980,719 A | 11/1999 | Cherukuri et al. | |
| 6,106,685 A | 8/2000 | McBride et al. | |
| 6,379,929 B1 | 4/2002 | Burns et al. | |
| 6,520,034 B1 * | 2/2003 | Masquelier et al. | ...... 73/863.21 |
| 6,532,835 B1 * | 3/2003 | Saaski et al. | ............ 73/863.21 |
| 6,565,727 B1 * | 5/2003 | Shenderov | ................... 204/600 |
| 6,629,826 B2 | 10/2003 | Yoon et al. | |
| 6,761,962 B2 | 7/2004 | Bentsen et al. | |
| 6,773,566 B2 * | 8/2004 | Shenderov | ................... 204/450 |
| 6,949,176 B2 | 9/2004 | Vacca et al. | |

(Continued)

FOREIGN PATENT DOCUMENTS

WO     05/100541 A2     10/2005

OTHER PUBLICATIONS

Gascoyne et al., "Dielectrophoresis-Based Programmable Fluidic Processors", *Lab Chip*, 2004, 4, pp. 299-309, The Royal Society of Chemistry, Published on web Jul. 1, 2004.

(Continued)

*Primary Examiner*—David A. Rogers

(57) ABSTRACT

The present disclosure relates to a method for sampling a fluid, such as air. As fluid flows through a device, a scrubbing liquid is positioned in a pattern to contact the fluid and constituents in the fluid are transferred to in the liquid.

22 Claims, 11 Drawing Sheets

U.S. PATENT DOCUMENTS

| | | | |
|---|---|---|---|
| 6,866,762 B2 | 3/2005 | Gascoyne et al. | |
| 6,893,547 B2 | 5/2005 | Gascoyne et al. | |
| 6,911,132 B2* | 6/2005 | Pamula et al. | 204/600 |
| 6,958,132 B2 | 10/2005 | Chiou et al. | |
| 6,989,234 B2* | 1/2006 | Kolar et al. | 435/6 |
| 2002/0043463 A1 | 4/2002 | Shenderov | |
| 2002/0168671 A1 | 11/2002 | Burns et al. | |
| 2002/0172969 A1 | 11/2002 | Burns et al. | |
| 2003/0006140 A1 | 1/2003 | Vacca et al. | |
| 2003/0012483 A1 | 1/2003 | Ticknor et al. | |
| 2003/0082081 A1 | 5/2003 | Fouillet et al. | |
| 2003/0164295 A1* | 9/2003 | Sterling | 204/450 |
| 2003/0183525 A1* | 10/2003 | Elrod et al. | 204/547 |
| 2003/0205632 A1 | 11/2003 | Kim et al. | |
| 2003/0224528 A1 | 12/2003 | Chiou et al. | |
| 2004/0007377 A1 | 1/2004 | Fouillet et al. | |
| 2004/0031688 A1 | 2/2004 | Shenderov | |
| 2004/0055536 A1 | 3/2004 | Kolar et al. | |
| 2004/0055891 A1 | 3/2004 | Vamsee et al. | |
| 2004/0058450 A1 | 3/2004 | Vamsee et al. | |
| 2004/0077074 A1* | 4/2004 | Ackley et al. | 435/287.2 |
| 2004/0091392 A1 | 5/2004 | McBride et al. | |
| 2004/0136876 A1 | 7/2004 | Fouillet et al. | |
| 2004/0231987 A1 | 11/2004 | Sterling et al. | |
| 2005/0056569 A1 | 3/2005 | Yuan et al. | |
| 2005/0115836 A1* | 6/2005 | Reihs | 204/450 |
| 2005/0179746 A1 | 8/2005 | Roux et al. | |
| 2006/0114296 A1* | 6/2006 | Gascoyne et al. | 347/73 |
| 2007/0131037 A1* | 6/2007 | Biegelsen | 73/863.21 |
| 2007/0224087 A1* | 9/2007 | Ding | 422/83 |

OTHER PUBLICATIONS

Lyuksyutov et al., "On-Chip Manipulation of Levitated Femtofroplets", *Appl. Phys. Lett.*, vol. 85, No. 10, pp. 1817-1819, Sep. 6, 2004.

Zeng et al., "Principles of Droplet Electrohydrodynamics for Lab-on-a-Chip", *Lab Chip*, 2004, 4, pp. 265-277, The Royal Society of Chemistry, published on web Jul. 1, 2004.

International Search Report and the Written Opinion of the International Searching Authority for Int'l application No. PCT/US06/04714 dated Jan. 22, 2008.

* cited by examiner

METHOD FOR FLUID SAMPLING USING ELECTRICALLY CONTROLLED DROPLETS

CROSS-REFERENCE TO RELATED APPLICATIONS

This application claims a priority benefit under 35 U.S.C. § 119(e) from U.S. patent application Ser. No. 60/651,865 filed Feb. 10, 2005 and U.S. patent application Ser. No. 60/680,914 filed May 13, 2005, both of which are incorporated herein by reference.

FIELD

The present teachings relate to gas sampling devices employing liquid droplets for collection of constituents such as, for example, airborne microorganisms and volatile organic compounds. The present teachings also relate to gas sampling devices employing ferrofluids. The ferrofluids may act as a transporting agent, sampling agent, scrubbing reagent, pump, valve, and a reactive reagent. Constituents and particles in a fluid immiscible with the ferrofluid may be captured in a magnetic field-induced ferrofluidic structure formed when the ferrofluid is subjected to a magnetic field. In various embodiments the fluid is a gas, for example air.

INTRODUCTION

Techniques for sampling air and other gas mixtures for analysis typically involve the collection of samples on solid surfaces. For example, it is known to use plastic bags (e.g., Tedlar) and metal canisters for collecting and importing a gas sample. In this manner, all constituents of the sample are collected for analysis. However, depending on the sampling procedure, volatile compounds have a tendency to "plate out" on the metal surfaces of the canister, while particles and pathogen aerosols tend to precipitate at the bottom. In addition, while the gas samples are collected onto a solid support, most assays, for example chemical and biological assays, are performed in a liquid phase. This may necessitate desorption and/or post-collection sample processing steps, which may result in sample loss and increased processing time.

Other known methods for analysis of particulate and aerosolized constituents include adsorption, cryotrapping, canister sampling, sedimentation, impaction on a solid surface, filtration, centrifugation, and electrostatic and thermal precipitation. While each of these methods may be suitable for trapping constituents, at least some of the methods may also require additional steps to isolate or concentrate the constituents.

Many of the sorbent-based methods are limited in their useful application, and tend to offer "one-shot," as opposed to continuous, analyses. For example, with thermal adsorption techniques there are no reanalysis resources for analyses exceeding instrument calibration range. Additionally, usually only "grab" samples can be taken. While sorbent tubes may be used to collect samples over extended periods of time, bag and canister samples are rarely collected in this manner.

In recent years, solid phase micro extraction has been widely used in the analysis of several contaminants in air in conjunction with gas chromatography (GC) methods, especially for volatile organic compounds ("VOCs"). Assuming a solid phase-coated fiber is exposed to a gaseous sample moving perpendicularly to the fiber axis for a period of time much shorter than the equilibrium time, the coating may behave as a perfect sink and all analytes reaching the fiber surface are immediately adsorbed. However, this method may not be effective for water-solvable or hydrophilic compounds.

Rain is an effective air cleaner, as it leaches and/or sweeps air particles such as microbial aerosols and VOCs from the atmosphere. The leaching and/or sweeping action is, at least in part, due to the air impinging on the rain droplets. The process is efficient at least because of a high surface-to-volume ratio at the liquid/gas interface. Impingement of a gas in a liquid is an effective way to collect a gaseous sample directly into a liquid format. For example, a gas stream or air bubble may be forced through a vessel containing, for example, teraglyme, water, and/or organic solvents, thereby effectively trapping at least one of particles, water-soluble constituents, and water-insoluble constituents. Typically, the gas is forced to bubble through large amounts of liquid, but there is little, if any, control of the gas-liquid interface. In addition, in known liquid impingement devices, large amounts of liquid are required for gas sampling. It could be desirable to provide a gas sampling device that takes advantage of efficiencies associated with liquid impingement while using a small amount of liquid.

SUMMARY

In various embodiments, the present teachings can provide a method for sampling a fluid, including providing a sampling fluid in a directional stream, positioning a scrubbing liquid in a pattern to intercept the sampling fluid, contacting the sampling fluid with the scrubbing liquid to remove at least one constituent from the sampling fluid, collecting the scrubbing liquid to collect the constituent, and analyzing the scrubbing liquid for the presence of the constituent, wherein the scrubbing liquid is positioned in the pattern by electrical control.

In various embodiments, the present teachings can provide a method for gas-sampling with a device comprising a first surface, a second surface parallel and proximate to the first surface, a volume at least partially defined by said first and second surfaces, a source chamber suitable for containing a liquid, said source chamber being fluidly connected to said volume, a collection chamber suitable for containing a liquid, said collection chamber being fluidly connected to said volume, and a passage allowing a flow of gas through said volume, wherein said device is capable of moving liquid droplets from the source chamber to the collection chamber.

In various embodiments, the present teachings can provide a gas-sampling device comprising a first surface comprising a plurality of electrodes arranged in a planar array, a second surface parallel and proximate to the first surface, a volume at least partially defined by said first and second surfaces, a source chamber suitable for containing a liquid, said source chamber being fluidly connected to said volume, a collection chamber suitable for containing a liquid, said collection chamber being fluidly connected to said volume, and a passage allowing a flow of gas through said volume.

In various embodiments, the present teachings can provide a process for sampling a gas, comprising allowing a gas to pass through a volume at least partially defined by a first surface and a second surface, parallel and proximate to said first surface, wherein a source chamber and a collection chamber, each of which is suitable for containing a liquid, is fluidly connected to said volume, transporting liquid droplets from the source chamber and across the first surface, and allowing the gas to impinge upon the liquid droplets disposed in said volume.

In various embodiments, the present teachings can provide a process for continuously monitoring a stream of gas for at least one of airborne biological and chemical warfare agents, said process comprising (a) allowing a gas to pass through a volume at least partially defined by a first surface comprising a plurality of electrodes arranged in a planar array and a second surface, parallel and proximate to said first surface, wherein a source chamber and a collection chamber, each of which is suitable for containing a liquid, is fluidly connected to said volume; (b) allowing the gas to impinge upon a liquid disposed in said volume; (c) continuously analyzing said gas for the presence of at least one of biological and chemical warfare agents; and (d) providing a feedback upon the detection of said agent. In various embodiments, the present teachings can provide a sampling device comprising a first surface; a second surface, parallel and proximate to the first surface; a cavity at least partially defined by said first and second surfaces; a plurality of magnetizable materials, each of which is shaped so as to provide two ends, wherein each end functions as one pole of a dipole when the material is magnetized, and wherein the ends oppose each other across said cavity; a power source configured to provide an electric current to said plurality of magnetizable materials in a manner that generates a magnetic field across said cavity; and a passage fluidly coupled with said cavity.

In various embodiments, the present teachings can provide a process for sampling a fluid, comprising applying a magnetic field to a ferrofluid, wherein said magnetic field has a magnitude sufficient to generate a magnetic field-induced structure from said ferrofluid; allowing a fluid to contact said magnetic field-induced structure for a period of time; removing the magnetic field; and analyzing the ferrofluid for the presence of a constituent.

In various embodiments, the present teachings can provide process for sampling a gas, comprising (a) applying a magnetic field to a ferrofluid, said magnetic field having a magnitude sufficient to generate a magnetic field-induced structure from said ferrofluid; (b) allowing a gas to pass through a cavity at least partially defined by a first surface and a second surface parallel and proximate to said first surface, wherein a source chamber and a collection chamber, each of which is suitable for containing a ferrofluid, is fluidly connected to said cavity; (c) allowing the gas to contact the ferrofluidic field-induced structure for a period of time; (d) removing or reducing the magnitude of the magnetic field in an amount sufficient to collapse the field induced structure; (e) transporting ferrofluid from the source chamber and across said first surface; and (f) analyzing the ferrofluid for the presence of a constituent.

It is to be understood that both the foregoing general description and the following description of various embodiments are exemplary and explanatory only and are not restrictive.

BRIEF DESCRIPTION OF THE DRAWINGS

The accompanying drawings, which are incorporated in and constitute a part of this specification, illustrate various embodiments. In the drawings.

Figure 1A:
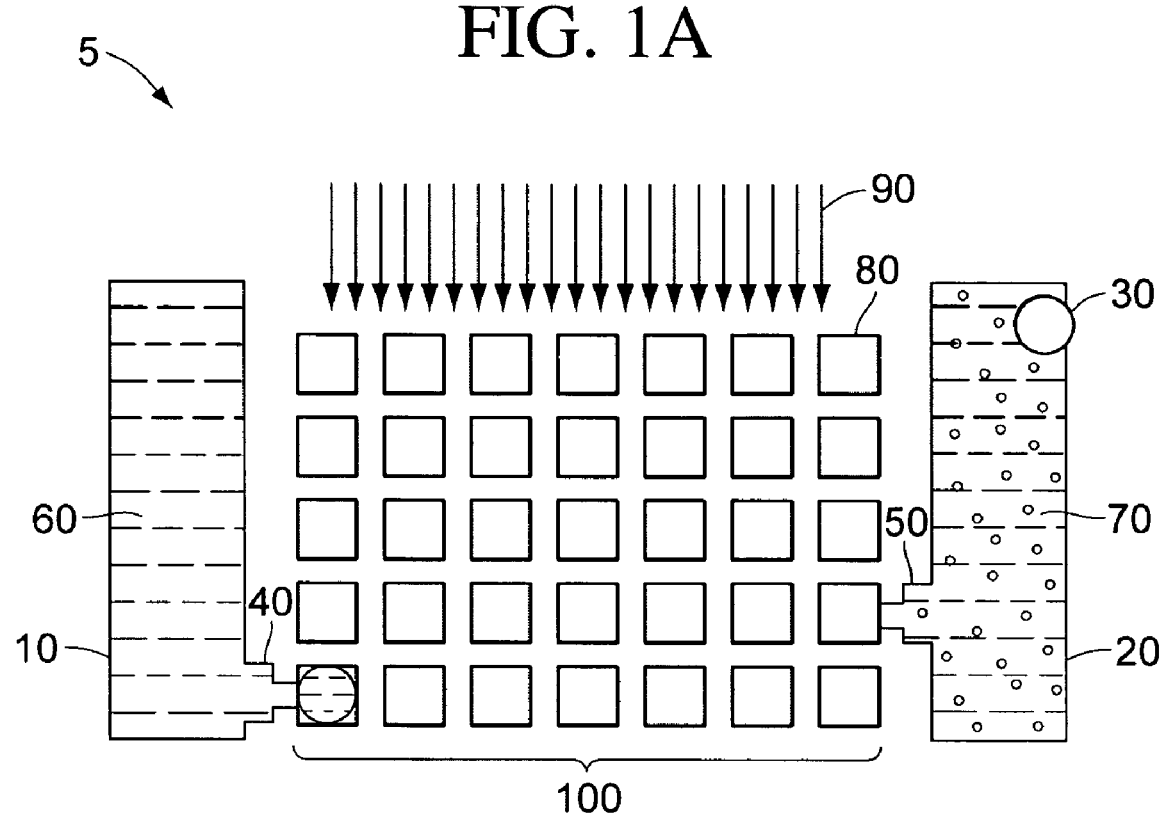
FIG. 1A illustrates a gas sampling device according to the present teachings.

FIG. 8 illustrates the effect of increasing field strength on a ferrofluid.

FIGS. 9A-H illustrate the operation of a sampling device according to the present teachings.

FIGS. 10A-E illustrate a sampling device according to the present teachings.

FIG. 11 illustrates the operation of a sampling device according to the present teachings.

FIG. 12 illustrates a sampling device according to the present teachings.

FIG. 13 illustrates a sampling device according to the present teachings.

DESCRIPTION OF VARIOUS EMBODIMENTS

Reference will now be made to various exemplary embodiments, examples of which are illustrated in the accompanying drawings. Wherever possible, the same reference numbers are used in the drawings and the description to refer to the same or like parts.

In various embodiments, any type of gas, such as air, may be sampled by the device disclosed herein. Alternatively, any type of fluid immiscible with the ferrofluid other than a gas such as air may be sampled. The gas may be pumped through the device or, alternatively, the device may be operated in environment in which the gas freely flows through the device. The device may sample a single gas or a mixture of gases. In various embodiments, the identity of the gas may be known but analytes therein, for example particulates, may be unknown.

In various embodiments, the device disclosed herein may be used in a number of applications. For example, the device may be associated with a medical device for sampling respirations of a mammal, for example human respiration. Such a device could be useful in monitoring lung function, as well as providing information on metabolic conditions. The device may be part of a portable device used for detecting chemical and biological warfare agents. The device may be used to monitor air quality in an environment in which chemical or biological weapons may be used. For example, it may be carried by soldiers and law enforcement professionals to periodically measure and sample air as a defense to a potential chemical or biological attack. In various embodiments, the device may be installed in a mask for periodic air sampling.

The device may also be used in a fashion similar to a smoke detector, whereby it is fixed in a dwelling and continuously monitors the air for potential harmful substances such as, for example, smoke, carbon monoxide, and/or radon. It may provide continuous feedback in the form of, e.g., illumination. The device may also provide an alert if a particular analyte and/or concentration of the analyte is detected.

In various embodiments, the device disclosed herein may be useful for various environmental applications. For example, the device may be used to detect and/or monitor the presence of air-borne pollutants in and around facilities known to generate air-borne pollutants, such as coal-fired utility boilers. By way of non-limiting example, such pollutants may include nitrogen oxides, sulfur oxides, hydrogen sulfides, unsaturated hydrocarbons, carbon dioxide, and mercury compounds, such as mercuric oxide. The device may be fixed in an environment in which dangerous substances are routinely handled, such as a laboratory or a chemical manufacturing facility. The gas sampling device disclosed herein may be incorporated alone or with other devices as a lab-on-a-chip.

The device may be situated in any location in which a fluid is to be sampled. For example, the device may comprise part of a conduit through which a fluid normally flows. As an illustration, it may be necessary to monitor a combustion product stream for the identification and/or quantification of substances, for example nitrogen oxides. The device disclosed herein can be integrated with, e.g., an exhaust stack. As another example, it may be desirable to monitor the purity of a supply stream, for example a stream of a reactant used in a chemical manufacture process. The sampling device disclosed herein may be integrated with a conduit delivering the reactant to, e.g., the reaction chamber.

Various types of substances in a gas, including particulates and volatile substances, may be retained and analyzed. The substances may be predetermined but of an unknown concentration, or both the identity and concentration of the substances may be unknown. The substances may be present in the gas in virtually any amount. This is due, at least in part, to the ability of the gas sampling device to transport liquid at variable speeds across a surface, thereby increasing its sorbtive capacity.

Suitable particulates may include organic and/or inorganic materials, debris, powders, metals such as airborne lead, spores, microbes, for example viruses, yeast, mold, pollen, airborne parasites, single-cell organisms, and bacteria. Airborne microorganisms or pathogens are typically sampled as aerosols, either as single, unattached cells or clumps of cells. The microbial aerosols may exist as either free-living organisms surrounded by a film of dried organic or inorganic material, or as cells attached to dust particles. The aerosol particulates may range in size from 1 to 50 $\mu$m. The gas sampling device may be effective on, e.g., a battlefield, since viruses or pathogens used in biological weapons may be delivered in aerosol form.

The volatile substances may include VOCs, for example benzene, tetrachloromethane, methylcyanide, and the like. Other substances may include gases, for example carbon monoxide, methane, carbon dioxide, and any number of organic and inorganic gaseous contaminants, including poisonous gases, and explosive vapors, such as natural gas and vapors associated with explosive devices that may be used in warfare, criminal or terrorist activities.

In various embodiments, the present disclosure relates to an apparatus for collecting at least one of airborne microorganisms, pathogens, particles, and molecules, for example VOCs, from a gas into liquid droplets. For example, when the ferrofluid is on the surface, liquid droplets may be transformed into magnetic field-induced ferrofluidic structures, such as pillars or columns, according to the direction and magnitude of applied magnetic field lines flowing through the ferrofluid. In various embodiments, droplets are moved from a source chamber, across a surface, and into a collection chamber. During this movement, a gas impinges upon the droplets or structures formed therefrom, and deposits, e.g., particles and/or VOCs therein, and the droplets are moved into the collection chamber. The particles and/or VOCs may then be subject to any one of collection, concentration, detection, analysis, or movement to an analytical device. The analytical device may be, for example, at least one of a CE/HPLC, GC, NMRor MS device. Suitable analytical devices also include those used for nucleic acid amplification (PCR, OLA, LNR, isothermal, etc.), and devices used for cytometry, cellular imaging, absorbance, and luminescence (fluorescence, chemiluminescence, bioluminescence, etc.).

In various embodiments, the gas sampling device transports liquid from a source chamber, across a surface over which a gas flows, and to a collection chamber. A second surface may be positioned parallel to and opposite from the first surface, and the two surfaces form a volume. The two surfaces may be positioned apart from each other at a distance ranging from 1 μm to 1 cm. For example, the distance may range from 10 μm to 1 mm. In various embodiments, the distance is 75 μm to 150 μm, for example 100 μm.

Passages may be positioned at opposite ends of the volume, allowing for the entry and exit of a gas, such as air, through the volume. As liquid is transported across the surface, a gas flows through the device and impinges upon the liquid. In various embodiments, a gas is forced through the device by, for example, a pump. In such instances, at least a portion of the gas is forced through the entry port, impinges upon the liquid, and flows out the exit passage.

In various embodiments, the air sampler devices disclosed herein may contain channels, for example ports, for delivering or receiving a fluid. The channels may be fluidly connected to at least one of the source chamber(s), collection chamber(s), analytical device(s), and liquid transporting surface(s). In general, the channels suitable for use in accordance with the present invention may be described as any volume through which a liquid may be transported. Suitable channels may be made of glass, and may optionally be transparent, or at least partially transparent. The channels may be constructed of any material suitable for containment of a given liquid, for example glass or a polymeric material. The channels may be of any dimension suitable for manipulating liquids in a desired manner, and in the case of microfluidic devices, may be microchannels. For example, according to various embodiments, the length, width and depth of the channels may range, independently, from 0.1 μm to 10 cm, for example, 10 μm to 1 cm. In the case of microchannels, the dimensions may range from 0.1 μm to 5 mm.

In various embodiments, the source and collection chambers suitable for use in the gas sampling devices disclosed herein include any space capable of containing a liquid and fluidly communicating with at least one channel. The chambers may be constructed of any material capable of holding a liquid, for example glass or a polymer. The chambers may be of any shape, for example they may independently be cylindrical, spherical, semi-spherical, or conical. The chambers may be of any size sufficient to hold the desired volume of liquid. For example, the chamber may range in size from 1 nanoliter to 1 liter.

In various embodiments, a flow meter, such as a gas flow meter, may be associated with the device. For example, a flow meter may be fixed, or positioned proximate to, at least one of the entry and exit ports. The flow meter may be electrically connected to a digital timer, so that the gas sample may be quantitatively analyzed. The timer may also be used to determine the time in which the liquid droplets sample the gas.

The flow meter/timer combination may permit accurate in-situ measurement of the gas sample. In addition the timer, alone or in combination with an integrated smart chip, may also control the flow of liquid from at least one source chamber. In this manner, the gas sample can be monitored continuously, with a continuous flow or repeated batches of liquid being metered onto the sample surface.

One of the many advantages of the sampling devices disclosed herein is the integration of sample collection and analysis. Prior art methods generally dictate that microbial and aerosolized samples are collected onto a solid support, but most bioassays and chemical assays are performed in the liquid phase. The present disclosure allows for collection of samples into a liquid, and the liquid may then be subjected to analytical methods.

In various embodiments, methods for analysis, e.g., detection of a substance in a gas, is incorporated in the sample collection chamber. For example, at least one of a fluorescent, calorimetric, and chemiluminescent assay can be performed in the collection chamber while the reagent is being delivered from a source chamber. Unlike other microfluidic digitation processes that require fluidic mixing and assaying on an electrode patch, various embodiments disclosed herein allow for the assays to be conducted in the traditional well/chamber format.

For example, liquid collected into a collection chamber may be analyzed in the chamber by a number of methods. For example, in various embodiments, at least a portion of a collection chamber is transparent to light of a selected wavelength. A mirror is disposed in the collection chamber. The liquid in the collection chamber is illuminated, and absorbance is measured. In other embodiments, analytical methods such as calorimetric, fluorescent, and chemiluminescent assays are performed in the collection chamber.

Alternatively, the liquid in the collection chamber may be distributed to an analytical device. For example, the liquid may flow through a channel (fluidly connected to the collection chamber) to any device suitable for conducting an analysis of a fluid. Non-limiting examples of suitable devices include GC, HPLC, IR, NMR, and MS devices. Suitable analytical devices also include those used for nucleic acid amplification (PCR, OLA, LNR, isothermal, etc.), and devices used for cytometry, cellular imaging, absorbance, and luminescence (fluorescence, chemiluminescence, bioluminescence, etc.).

In various embodiments, the devices disclosed herein contain multiple source chambers. The source chambers contain, independently, at least one of a scrubbing liquid, a solvent, and an assay reagent. A "scrubbing liquid" refers to a liquid having an affinity for an analyte that may be present in a fluid, such as a gas. For example, a composition including teraglyme and water may have an affinity for certain VOCs. Another example is a ferrofluid capable of functioning as a scrubbing liquid. A solvent can be any liquid, such as water, in which a scrubbing liquid and/or an assay reagent is dissolvable. The assay reagent may be any reagent suitable for detecting at least one of the presence and concentration of a species in a gas. In various embodiments, the assay reagent is dispensed from a source chamber and is transported across a surface over which a gas sample flows. The assay reagent binds with a constituent in the gas, is pooled in the collection chamber, and is subjected to a gas and/or liquid phase analysis. In various embodiments, the assay reagent is also capable of functioning as the scrubbing liquid, and vice versa.

The term "pattern" as used herein refers to the arrangement of the scrubbing liquid to increase the surface area of contact with the fluid to be scrubbed. Examples of patterns are provided herein, including liquid droplets aligned in a checkerboard array or ferrofluid structures such as pillars. Patterns are not limited to these examples and can be any shape or dimension such that surface area is increased, for example coating the internal surface area of a cavity or creating a lattice.

The term "electrical control" as used herein refers to the capability of positioning the scrubbing liquid into a pattern. It can also refer to positioning the scrubbing liquid out of a pattern. For example, the scrubbing liquid can be contained in a source chamber and can be positioned into a pattern with electrical control, held in that pattern during scrubbing with electrical control, and collected out of the pattern into a collection chamber with electrical control.

In various embodiments, the droplets may be moved from the source chamber, across a surface, and to a collection chamber by a number of different methods. For example, the droplets may be moved by at least one of electrowetting (EW), electrowetting on dielectric (EWOD), dielectrophoresis, ferrofluidic flow, diamagnetic levitation of droplets, and acoustic levitation of droplets. Any process suitable for moving a liquid across a surface may be used in accordance with the present disclosure.

There are a number of advantages attendant with using liquid droplets as air sampling media. For example, liquid droplets may provide greater surface area. As a result, a large amount of a gas may be sampled using mere microliters of liquid. According to various embodiments, it may be advantageous to exploit the distribution of liquid surface at the liquid/gas interface, and the interface of the liquid surface area to the solid surface area. As a droplet, or an array of droplets is manipulated by a control element operating at the liquid/solid interface, the liquid surface exposure to air or gas phase will also change dynamically. Since a small amount of liquid is capable of being spread onto a solid surface as droplets, or a pattern of droplets, there is a large amount of liquid surface area created due to the increase of surface-to-volume ratio. Thus, in various embodiments, a portion of the liquid surface is in contact with a solid surface used to control the liquid movement, while the other portion of the liquid surface is in contact with a gas to be sampled.

The interaction between the liquid and the gas sample stream can take several different forms such as, for example, chromatographic interactions at the liquid/gas interface; filter-like interaction (an aerosolized particulate cannot pass through the interstitial spaces between liquid droplets); direct capture (an aerosolized particle directly impacts a liquid droplet); and charge interactions on the charged surface of the liquid droplet.

In various embodiments, the liquid is spread across a solid surface as a pattern of droplets. For example, the droplets may be patterned in a two-dimensional array on the solid surface, and a gas flows through the interstitial space of the droplets. It may be advantageous to increase capture efficiency by minimizing the interstitial space between the droplets.

In accordance with one aspect of the present disclosure, liquid droplets may be moved across a surface by a phenomenon known as electrowetting. This technique uses electric fields to effect fluid movement by relying on the ability of those fields to change the contact angle of the fluid on a surface that is initially resistant to the flow of a liquid. The term "contact angle" describes the angle formed as a result of contact between a fluid and a solid surface. It reflects the interfacial affinity between the fluid and the solid surface, i.e., the wettability of the surface with respect to the fluid.

When an electric field gradient is applied to a droplet on a fluid-transporting surface, different contact angles are formed between leading and receding surfaces of the droplet with respect to the fluid transporting surface. This imbalance in surface tension forces will produce a net force that moves the droplet.

For example, in the case of a polar liquid droplet, such as a droplet of an aqueous liquid, the application of an electric potential difference across the liquid-solid interface reduces the contact angle, thereby effectively making the surface more hydrophilic. In various embodiments, the electrical potential difference effecting the hydrophilic-hydrophobic conversion is controlled by closing a circuit to at least one electrode arranged on an individually addressable electrode array. Such an array can be programmed to generate an electric field in a predetermined manner. The array permits the manipulation of droplets on, for example, a lab-on-a-chip. The manipulation may include at least one of droplet generation from a stream or body of liquid, droplet translocation, droplet fusion, and droplet fission.

In various embodiments, the surface over which the gas flows will contain at least one electrode, for example multiple electrodes. The electrodes may be of any material and dimensions suitable for moving a fluid by electrowetting. For example, the electrodes may be thin metal films, patterned using any thin film deposition process known in the art. The electrodes may be made from any conductive material such as, for example, copper, gold, platinum, aluminum, and conducting polymers, including polymers that are conducting per se, and conducting composites containing a non-conducting polymer and a conducting material such as a metal or a conducting polymer. The electrodes may be of any dimension suitable for transporting a liquid by EW or EWOD. For example, the electrodes may range in size from 10 µm to 5 mm on each side. In various embodiments, the edges of the electrodes have interdigitated sawtooth or meander outlines.

In various embodiments, the electrodes are provided as a two-dimensional matrix array. Such an array allows movement of the fluids by electrowetting in any direction on the substrate. The matrix array may comprise 4 to 10,000 individually addressable electrodes. The electrodes may be flush, or may be spaced apart by a gap. The gap may range in size from 1 µm to 500 µm. The gas sampling device disclosed herein contains a volume formed by two parallel and opposing surfaces. One surface may contain the array of electrodes, and the opposing surface may contain a ground electrode.

When a liquid droplet is in direct contact with an electrode, the applied voltage may be limited by the possibility of electrolyzing the liquid. However, an insulating layer may be inserted between the droplet and the electrode to accommodate a high applied voltage without electrolysis. This is referred to as electrowetting on dielectric (EWOD), and it permits the application of a high-strength wetting force that would otherwise electrolyze a droplet in direct contact with an electrode.

In various embodiments, the insulating layer is comprised of any material capable of electrically insulating the electrode. Depending on the choice of materials, it may be advantageous for the electrically insulative layer to also be chemically insulative. The chemically insulative layer may function to protect the surface from potentially corrosive effects of a liquid. According to various embodiments, it could be advantageous for the insulative layer to be made hydrophobic. This may be accomplished by selecting a hydrophobic insulative layer. Alternatively, it may be accomplished by making the insulative layer hydrophobic by, for example, binding a hydrophobic moiety to the surface. Exemplary hydrophobic moieties include silanes, siloxanes, fluorosilanes, fluorosiloxanes, hydrocarbons, fluorocarbons, combinations thereof, and polymers and copolymers of any of the foregoing.

Any material capable of providing an electrically and/or chemically insulative layer may be used in accordance with various embodiments. For example the insulating layer may be composed of silicon oxide, silicon nitride, silicon oxynitride, tantalum oxide, polymers such as Parylene, Dupont Teflon AF, 3M Fluorad, 3M EGC 1700, other fluoropolymers, polysiloxanes, and carbon. The thickness of the insulative layer may range from 0.1 µm to about 200 µm.

In various embodiments, the electrodes and/or insulative coatings thereon may be textured as a way of potentially manipulating charge density. For example, the topography of the surfaces may be altered. The surface modification may involve increasing or decreasing surface roughness. Such modifications may be conducted by any known additive or subtractive methods, including depositioning, masking, and etching processes.

In various embodiments, the liquid droplets may be transported across a surface of the gas sampling device disclosed herein by optical activation. In such an embodiment, a photoconductive material is electrically connected to both an electrode and the insulative coating. For example, the photoconductive material is disposed between the electrode and the insulative coating. The photoconductive material is activatable by directed light to provide an electrical potential difference across the insulating layer.

In various embodiments, the photoconductive material used in the devices disclosed herein corresponds to a material with a dark conductivity ranging from $10^{-5}$ to $10^{-12}$ $\Omega^{-1} \cdot cm^{-1}$. The photoconductive material exhibits relatively low conductivity when dark, and relatively high conductivity when illuminated by a light source. In various embodiments, an example of a suitable photoconductive material is amorphous silicon, which has a dark conductivity of approximately $10^{-8}$ $\Omega^{-1} \cdot cm^{-1}$. In various embodiments, light with a wavelength ranging from 400 nm to 1100 nm is used to illuminate at least portions of the amorphous silicon. The light intensity for activating the gas-sampling device can be low. For example, a light intensity that may be suitable for switching amorphous silicon is 65 mW/cm$^2$. The layer of photoconductive material permits optical control of an electrical potential difference across a corresponding portion of the device. Optical activation of EW and EWOD devices is further discussed in U.S. Pat. No. 6,958,132 to Chiou et al., the disclosure of which is incorporated herein by reference in its entirety.

In various embodiments, as in the case of an EW or EWOD device, any type of liquid capable of being transported across a surface may be employed in the gas sampler disclosed herein. Often, the selected liquid is aqueous. Thus, where the liquid transporting surface is hydrophobic, an aqueous liquid may be used. It may be suitable to employ a liquid having an affinity for a specific element of interest in the gaseous stream.

The choice of liquid may depend, at least in part, on the identity of constituents to be sampled. For example, when the constituents are unknown, it may be advantageous to use water because water is known to collect most air particles, such as dust, contaminants resulting from exhaust, microbial aerosols, and water-soluble VOCs like PCB and nitroaromatic compounds. Alternatively, the constituent may be known, and the liquid is chosen accordingly. For example, in the case of VOCs, it may be suitable to use a teraglyme/water mixture, since such a mixture has a known affinity for a variety of VOCs.

Figure 1B:
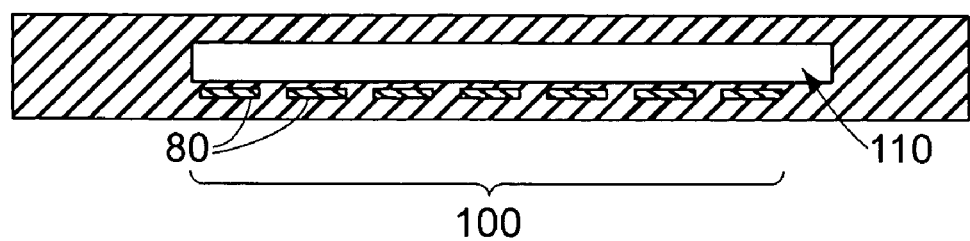
FIG. 1B illustrates a cross-sectional view of a gas sampling device according to the present teachings.

FIG. 1a illustrates a gas sampling device 5 in accordance with various embodiments. The device contains a source chamber 10 suitable for containing a liquid 60, and a collection chamber 20 suitable for containing a liquid 70 upon which a gas has impinged. Collection chamber 20 may contain a sample collector 30. The sample collector may be a port to an analytical element such as, for example, a GC column. The gas sampling device further contains a port 40 through which liquid 60 is permitted to flow onto surface 100. Surface 100 contains an individually addressable array of electrodes 80. The array may be used to shape an electric field surrounding a droplet and create a spatial variation in the electric force density, thereby effecting droplet generation, translocation, fission, and fusion. Gas 90 flows through an opening in device 5, and impinges upon liquid 60 as the liquid is moved across surface 100 to port 50. FIG. 1b illustrates a cross-sectional view of device 5. Gas flows through opening 110 and over a surface 100, under which electrodes 80 are present.

Figure 1C:
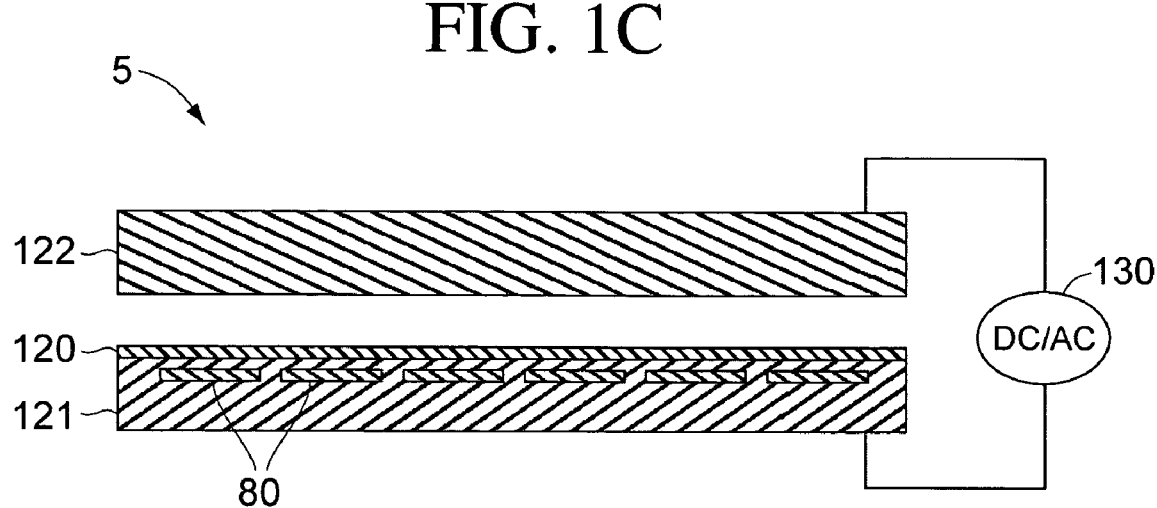
FIG. 1C illustrates a cross-sectional view of a portion of gas sampling device, including a power source, according to the present teachings.

FIG. 1c illustrates another cross-sectional view of device 5, including a dielectric coating 120 and a power source 130 configured to provide an electrical potential difference. Plate 121 contains an array of electrodes 80. Plate 122 may contain at least one ground electrode. In various embodiments, the power source 130 may be chosen from any source suitable for providing a sufficient electrical potential difference across a liquid in a volume formed by the two plates. For example, the power source may be configured to provide an alternating voltage source.

The voltage and frequency characteristics may be chosen according to the materials used in the surface 100 and/or a device in which the sampler is situated, and may also be chosen in accordance with the properties of the liquid 60. The magnitude of the AC voltage source can vary according to the properties, e.g., the thickness, of the materials used to construct the surface 100. In various embodiments, the AC voltage source can supply an electrical potential difference ranging from 10 volts to several hundred volts, with a frequency ranging from 10 Hz to 500 kHz. In one embodiment, the AC voltage source is connected to the surface 80 with only two leads. In another embodiment, the AC voltage source is inductively connected such that no electrical leads are required.

Figure 2A:
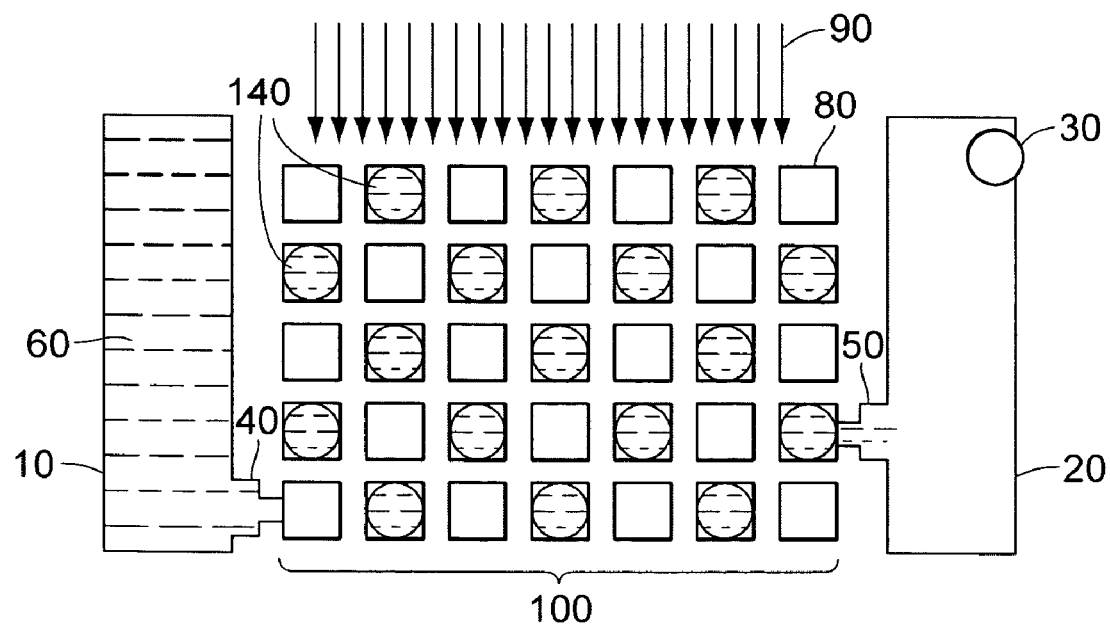
FIG. 2A illustrates the operation of a gas sampling device according to the present teachings.
Figure 2B:
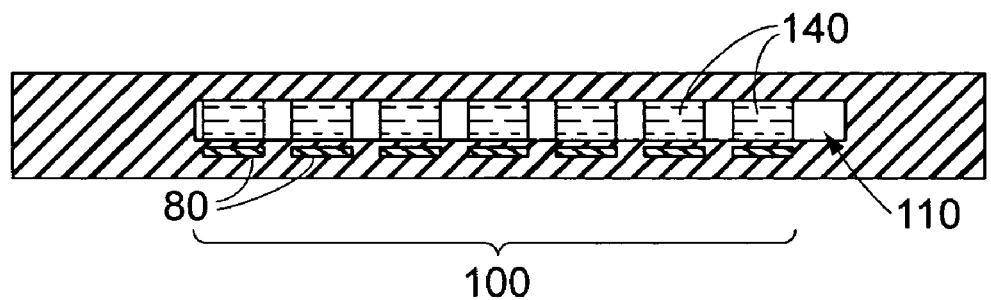
FIG. 2B illustrates a cross-sectional view of the operation of a gas sampling device according to the present teachings.
Figure 2C:
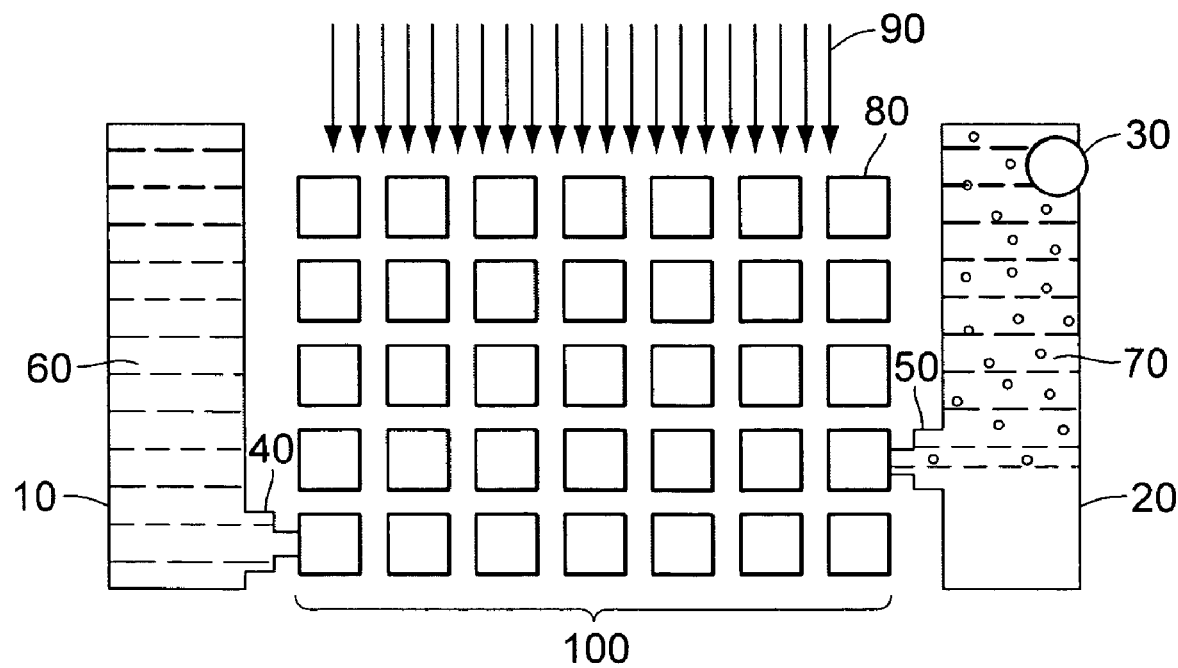
FIG. 2C illustrates the operation of a gas sampling device according to the present teachings.

The operation of device 5 may be illustrated with reference to FIG. 2. In FIG. 2a, scrubbing liquid 60 is dispensed from source chamber 10 onto surface 100. By alternately applying current to individual electrodes 80, the liquid may be patterned as droplets 140 onto surface 100. Gas 90 is permitted to flow past droplets 140 such that the gas impinges upon the droplets and deposits, for example, particles and/or VOCs onto the droplets. The droplets continue to move across surface 100 by alternately applying electric current to the electrodes. The droplets are subsequently moved from the surface to port 50. FIG. 2b illustrates a cross-sectional view of the device 5, with liquid droplets 140 patterned on surface 100. As shown in FIG. 2c, the liquid is subsequently collected in collection chamber 20.

Figure 3:
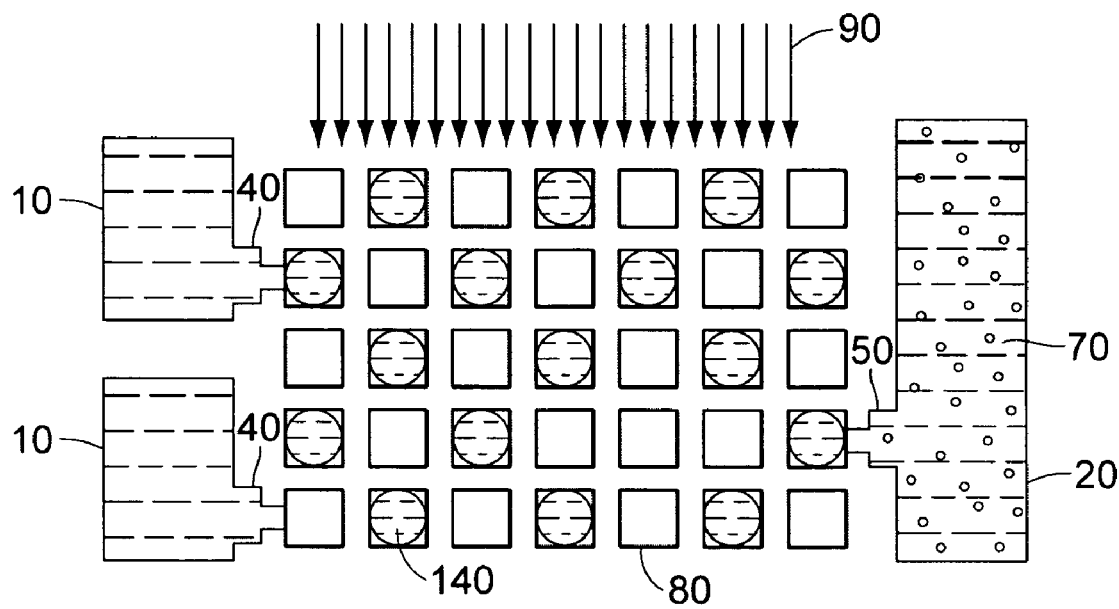
FIG. 3 illustrates a gas sampling device, including multiple source chambers, according to the present teachings.

FIG. 3 illustrates another embodiment of the present disclosure. Two source chambers 10 are fluidly connected to surface 100. This enables the device to operate with two types of liquids. According to various embodiments, more than two source chambers might be used. There are a number of reasons why it might be desirable to used more than one type of liquid. For example, two scrubbing liquids might be used because each has an affinity for different types of gaseous particles. For example, an aqueous system may be used to collect particles and/or water-soluble VOCs, whereas a non-aqueous liquid may be employed to collect water-insoluble VOCs.

In various embodiments, it may be desirable to provide a scrubbing liquid in one source chamber, and a reagent in a separate source chamber. The reagent may be employed as, e.g., a binding agent capable of binding to a substance of interest in the gas. The bound reagent is then driven into the collection chamber 70 and subjected to an assay to determine, e.g., the presence and concentration of a substance of interest in the gas. In various embodiments a sampling device contains two source chambers each containing a reagent. In various embodiments, the reagents themselves function as scrubbing liquids. Once the reagents are driven into the collection chamber, they may be analyzed to determine the presence and concentration of a substance, or substances, of interest.

Figure 4:
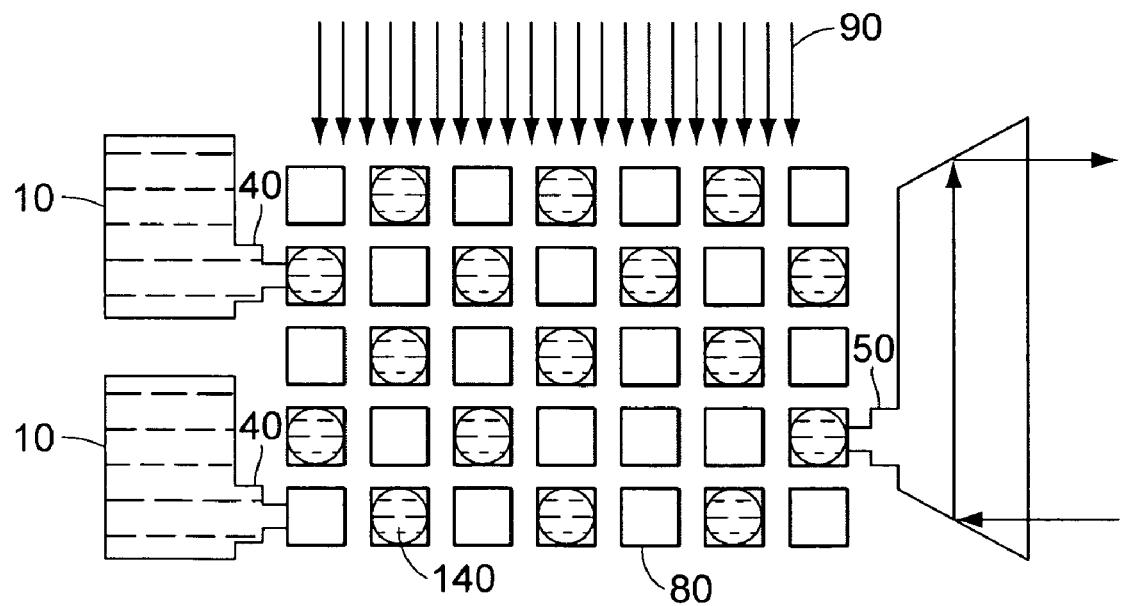
FIG. 4 illustrates a gas sampling device, including a specialized collection chamber, according to the present teachings.

As shown in FIG. 4, a detection element comprising a mirror can be incorporated into the device. In this embodiment, the collection chamber contains a mirror on the internal chamber wall nearest surface 100. At least a portion of the opposing wall may be transparent to allow light transmission. Light is introduced into the chamber and reflected from the mirror. Absorbance can be measured to determine, e.g., the concentration of a particular analyte in the collected liquid.

Figure 5:
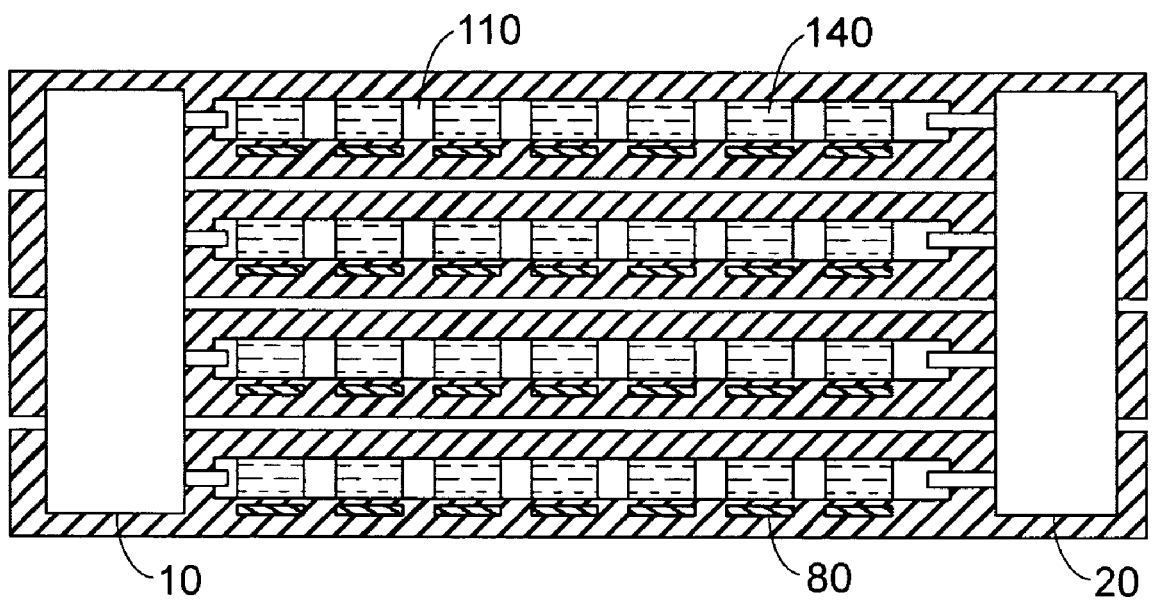
FIG. 5 illustrates an array of gas sampling devices according to the present teachings.

In various embodiments, multiple air sampling devices can be combined into a single device. For example, the devices can be arranged as illustrated in FIG. 5. Four air sampling devices are fluidly connected to a common source chamber and a common collection chamber. This arrangement may allow for an increased gas flow rate. In addition, the arrangement may allow for greater capture efficiency of at least one of aerosols, partials, and gaseous constituents.

In various embodiments, other components may be installed on the devices disclosed herein. For example, the device may contain a flow meter, or multiple flow meters, for measuring the volume of gas sweeping through the device.

In various embodiments, the ferrofluid is moved from a source chamber to a surface. A magnetic field is applied, and the ferrofluid responds by forming field-induced ferrofluidic structures, such as columns or pillars. A gas contacts the formed structures and deposits, for example, at least one of particles, aerosols, and VOCs therein. Once at least a portion of the magnetic field is removed, the ferrofluid reverts to the liquid phase and is transported to the collection chamber.

There are a number of advantages attendant with using ferrofluids as gas-sampling media. For example, the solid field-induced structures may provide a greater surface area in comparison to the liquid phase. As a result, a large amount of a gas may be sampled using mere microliters of ferrofluid. As a volume of ferrofluid is manipulated by a magnetic field, the ferrofluid surface exposure to a gas can change dynamically. Since a small amount of ferrofluid is capable of being shaped into field-induced pillars, a large amount of surface area may be created due to the increase in surface-to-volume ratio. Thus, in various embodiments, a portion of the ferrofluidic field-induced structure is in contact with a surface of the sampling device, while the other portion of the structure is in contact with a gas to be sampled.

The interaction between the ferrofluid and the gas sample stream can take several different forms such as, for example, chromatographic interactions at the solid/gas interface; filter-like interactions (an aerosolized particulate cannot pass through the interstitial spaces within and/or between the magnetic field-induced structures); direct capture (an aerosolized particle directly impacts a field-induced structure); and charge interactions on the charged surface of the field-induced structure.

In various embodiments, a "ferrofluid," also known as a "magnetic liquid," refers to a liquid that responds to magnetic attraction. According to one embodiment, a ferrofluid is a liquid comprising a colloidal dispersion of magnetic particles, such as magnetite ($Fe_3O_4$). A ferrofluid exhibits properties that make it useful in devices where fluid properties and resistance to gravity are desirable. A ferrofluid changes its viscosity, shape, and apparent density in response to the strength of the applied magnetic field. For example, a ferrofluid will take on the three-dimensional shape of a magnetic field passing through it. That is, the ferrofluid can follow the magnetic field lines imposed on a "liquid format" of a magnet. The physical, chemical, and biochemical characteristics of said ferrofluid can be varied as long as the magnetic and fluidic properties remain.

The magnetic particles in a ferrofluid may be nanoscale, for example from 1 to 100 nm in diameter. According to various embodiments, the particles have a diameter ranging from 1 to 20 nm, for example 10 nm. If the magnetite particles are too large, they may not exhibit colloidal properties, but instead exhibit the properties of a powder. If the particles are too small, they may not be sufficiently affected by the presence of a magnetic field. An additional distinction between a liquid containing micro-scale magnetic particles and a ferrofluid containing nano-scale size magnetic particles is that the ferrofluid is a colloid, in which the nano-scale magnetic particles are not easily separable from solvents in which they are suspended.

In various embodiments, the magnetic particles are dispersed in a liquid. The liquid may be chosen from organic and inorganic solvents, for example water, alcohols, hydrocarbons, and oils. Ferrofluids may be prepared by grinding magnetite in a solvent. Grinding may be conducted in the presence of soap. The soap will coat the particles with an oil-like surface film. If the particles are of a certain size and have a sufficient coating, they will disperse in a liquid and will not settle, or at least not substantially settle out of solution. Ferrofluid compositions are discussed in U.S. Pat. Nos. 5,879,580; 5,851,416; 5,667,716, and 5,656,196.

Figure 6A:
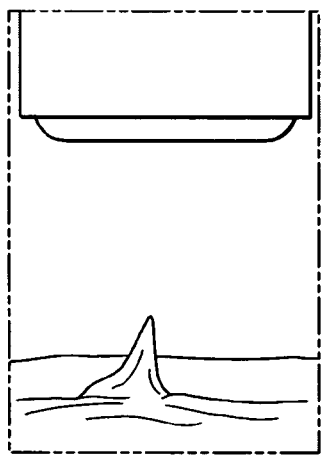
FIGS. 6A-6C illustrate the behavior of a ferrofluid in the presence of magnetic fields of increasing strength.
Figure 6B:
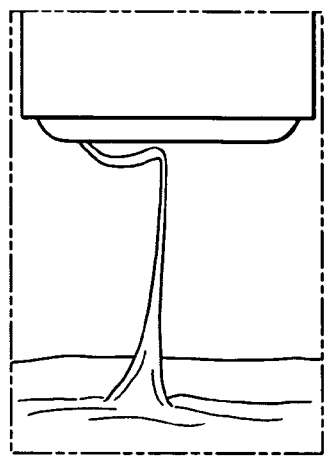
Figure 6C:
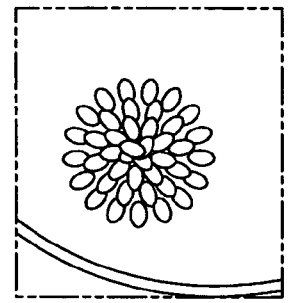

When a ferrofluid is placed in a magnetic field, it can be shaped by the conflicting attractions of gravity, magnetism, and surface tension. FIG. 1 demonstrates the behavior of a ferrofluid in a magnetic field. A drop of ferrofluid was placed on a glass sheet with yellow paper underneath for photographic contrast. Seven small magnets were placed below the paper. As the bundle of these seven magnets approached the bottom of the ferrofluid, the magnetic field increased (FIG. 6A). In regions of lower magnetic field strength the ferrofluid remained a liquid, forming flat drops within the conflicting forces of gravity, cohesion, and magnetic forces (FIG. 6B). In regions of relatively high magnetic field strength, the fluid broke into spikes in a manner suggestive of the way iron filings tend to line up in columns when subjected to a magnetic field (FIG. 6C). The magnetic forces acting upon the ferrofluid here are relatively small, in the range of 5 to 1500 Gauss. The magnetic field of the earth is approximately 0.5 Gauss, and a small magnetic bar generates a field of approximately 100 Gauss. An electromagnetic coil may easily generate a magnetic field in the range of several thousand Gauss, which can be used to drive a ferrofluid as a pump, valve, seal, dumper, etc.

In various embodiments, the sampling device disclosed herein may contain a pair of flat substrates placed in parallel to each other to create a cavity. The substrates may be comprised of any material suitable for containing a ferrofluid, for example glass or a polymeric material. In various embodiments, each substrate will have embedded therein a material capable of generating a magnetic field. In various embodiments, the material is a magnetizable material such as iron or cobalt. The magnetizable material can be electrically connected to a power source. In various embodiments, the magnetizable material is shaped so as to provide two opposing ends functioning, upon magnetization, as opposite (e.g., North and South) poles of a magnet, with each pole embedded in opposing substrates. With reference to the magnetizable material 1010 in FIG. 7, there is provided a magnetizable bar of iron 1015 electrically connected by conductive wire 1050 to a power source. This configuration allows (upon the application of an electric current) for the generation of a uniform magnetic field at the gap 1040 between the opposing poles 1020 and 1030, with the gap approximating the distance between the two parallel substrates of the gas sampling device. A plurality of magnetizable materials can be embedded in opposing substrates to provide an array of opposing poles across the volume formed by the opposing substrates.

The distance between the two substrates may vary. The distance may be selected based on the properties of the ferrofluid and the ability of the device to generate a magnetic field of varying strength. For example, the two surfaces may be positioned apart from each other at a distance ranging from 1 μm to 10 cm. For example, the distance may range from 10 μm to 1 mm. In various embodiments, the distance is 75 μm to 150 μm, for example 100 μm.

Figure 8:
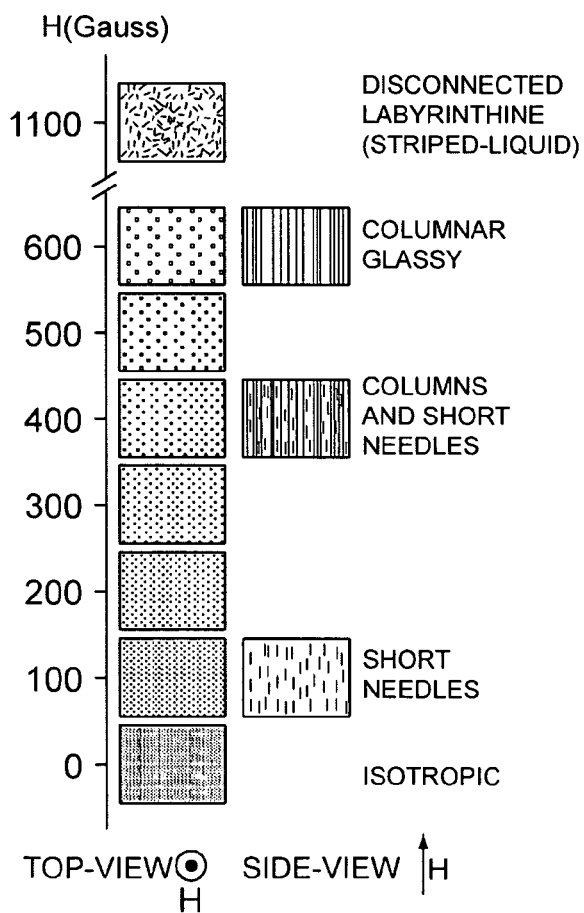

In various embodiments, the ferrofluid bounded by the two substrates may form magnetic field-induced structures that vary according to the strength of an applied magnetic field. This phenomenon is illustrated in FIG. 8. A ferrofluid is placed between a pair of flat substrates in parallel with each other. A magnetic field is applied. The ferrofluid follows the magnetic field lines and concentrates in these lines when the field strength is increased to a certain level. As the strength of the magnetic field increases, the ferrofluid is transformed from a liquid (0 Gauss) to magnetic field-induced columns (600 Gauss). In various embodiments, in the gas-sampling device disclosed herein, a gas contacts the field-induced structures and deposits, e.g., contaminants and/or VOC's into those structures. After a period of time the ferrofluid is permitted to return to the liquid phase, is transported to a collection chamber, and its contents are analyzed for the presence and/or concentration of the analytes and/or VOCs.

The gas-sampling devices disclosed herein may be constructed as what may be referred to as one and two-dimensional structures. In a "one-dimension" structure, magnetic dipoles are arranged along a single axis drawn between the source and collection chambers. In a "two-dimension" structure, the dipoles are arranged in a two dimensional array between the source and collection chambers.

Figure 9A:
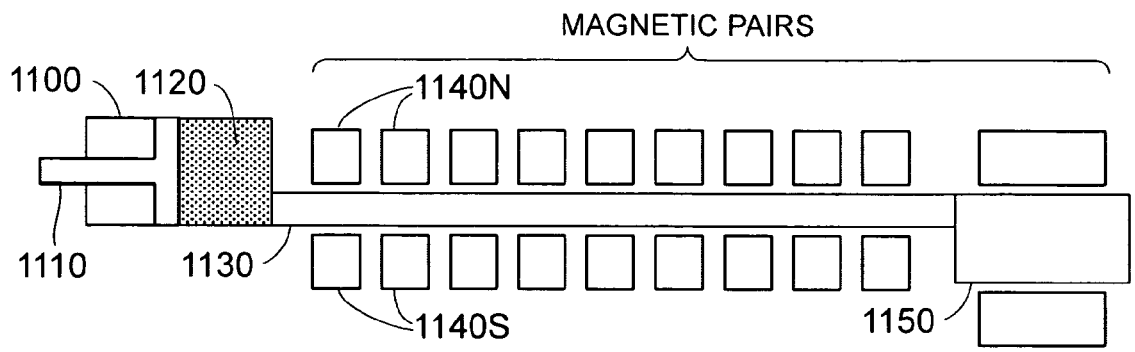

FIGS. 9A-9H illustrate a configuration and proposed operation of a "one-dimensional" gas sampling device in accordance with the present disclosure. With reference to FIG. 9A, there is provided a source chamber 1100, an optional piston 1110, and ferrofluid 1120. Collection chamber 1150 is fluidly connected to source chamber 1100 by channel 1130. Dipoles of a single magnet or opposite poles (North vs. South, South vs North) of two magnets are arranged along the length of channel 1130, such that the North pole 1140N is on the opposite side of channel 1130 from the South pole 1140S.

Figure 7:
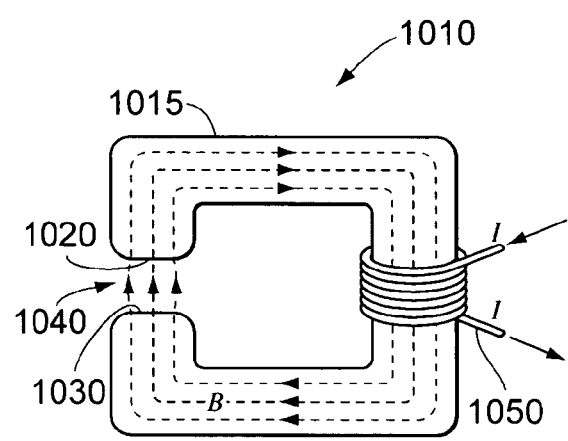
FIG. 7 illustrates a device useful for generating a magnetic field.

In various embodiments, one method for generating a uniform magnetic field comprises the use of two permanent magnetic bars placed against each other. The strength and magnitude of the magnetic field can by manipulated by varying the distance between the two bars. According to another method, a magnetic field may be variably applied to a gap between two poles by switching on and off a power source supplying electrical current to a magnetizable bar (e.g., cobalt or iron) shaped such that two ends of the bar oppose each other across a gap (as illustrated in FIG. 7). For the purposes of the present disclosure, a dipole is said to be "switched off"

when there is no, or substantially no, electrical current supplied to the magnetizable material. Conversely, a dipole is said to be "switched on" when sufficient electrical current is supplied to the magnetizable material to generate a magnetic field.

Figure 9B:
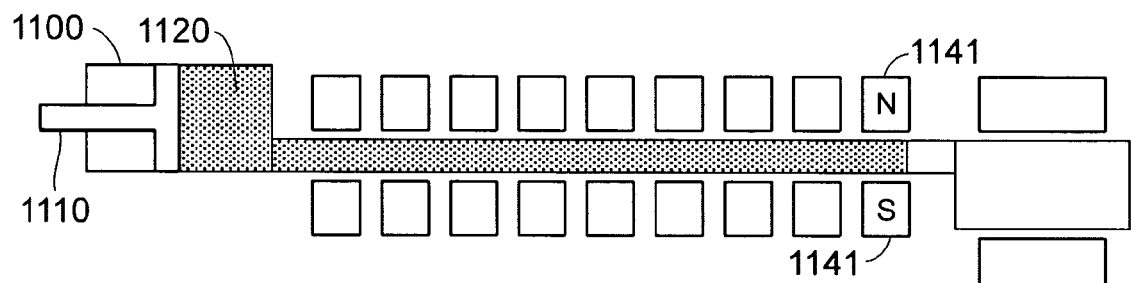
Figure 9C:
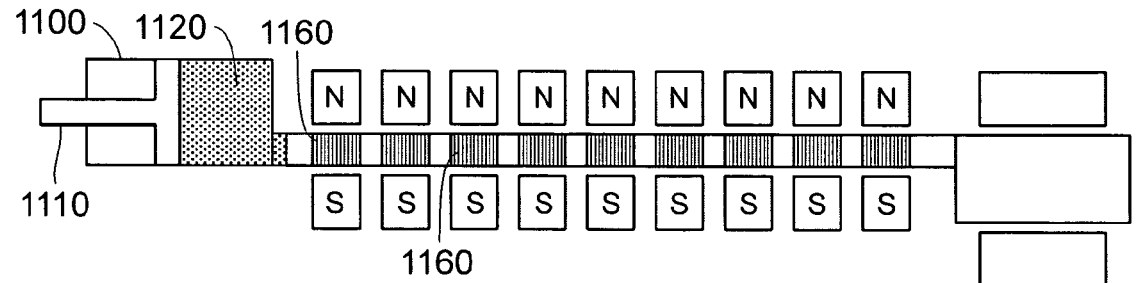
Figure 9D:
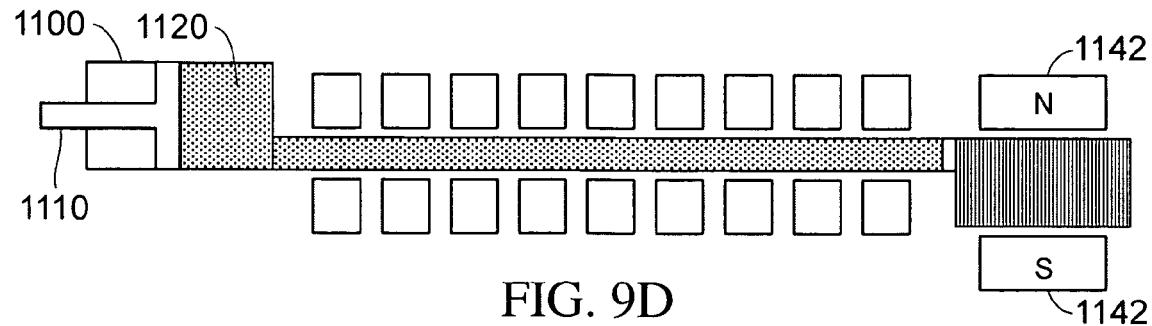

Operation of the two-dimensional device may commence by activating a combination of pressure and magnetic forces as illustrated in FIG. 9B. Simultaneously, (A) piston 1110 is actuated to force ferrofluid from source chamber 1100 into channel 1130, and (B) dipole 1141 is switched on. This has the effect of drawing ferrofluid from source chamber 1100 into channel 1130. In FIG. 9C, actuation of the piston is halted and the remaining dipoles are switched on, thereby providing magnetic fields across channel 1130. The magnetic fields are of sufficient strength to generate magnetic field-induced structures in the ferrofluid, in this case columnar structures 1160. A gas is permitted to flow through (e.g., in a direction perpendicular to the magnetic field lines) and contact the ferrofluidic pillars, depositing constituents therein. After a period of time, and as illustrated in FIG. 9D, the dipoles arranged along channel 1130 are switched off, thereby collapsing the ferrofluidic pillars, and dipole 1142 is switched on. Simultaneously, piston 1110 is actuated to force ferrofluid from channel 1130 into collection chamber 1150.

Figure 9E:
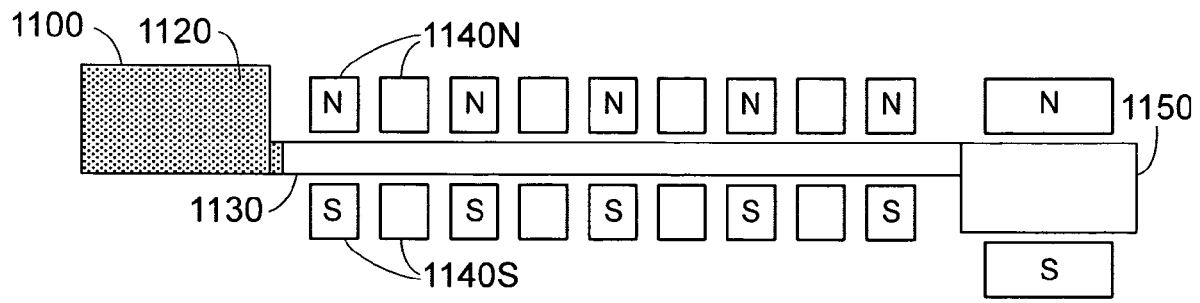
Figure 9F:
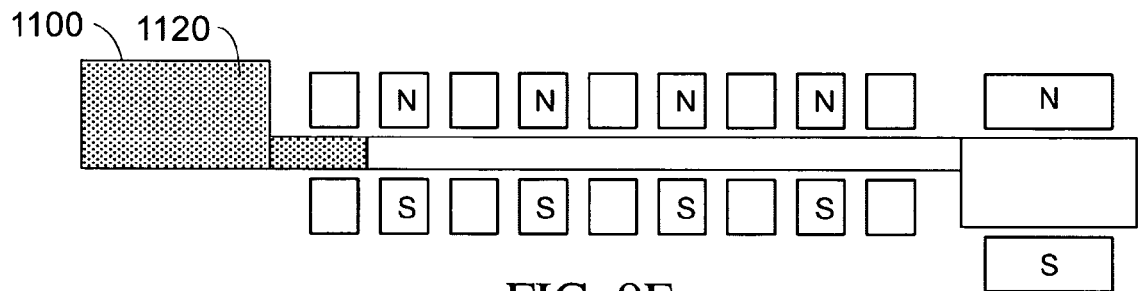
Figure 9G:
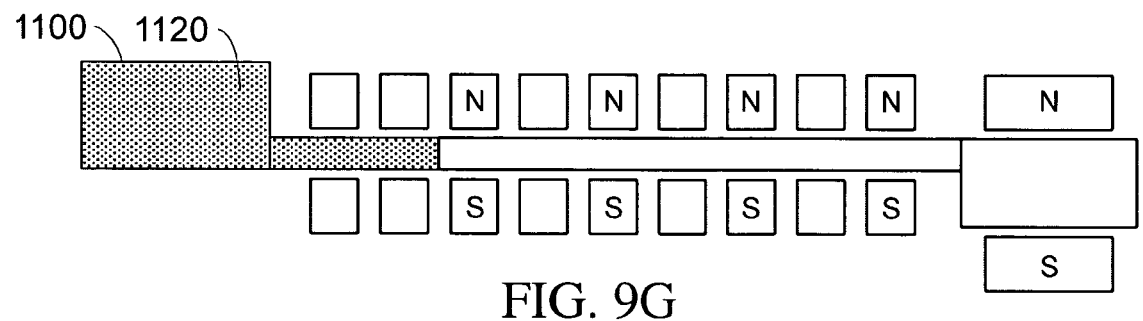
Figure 9H:
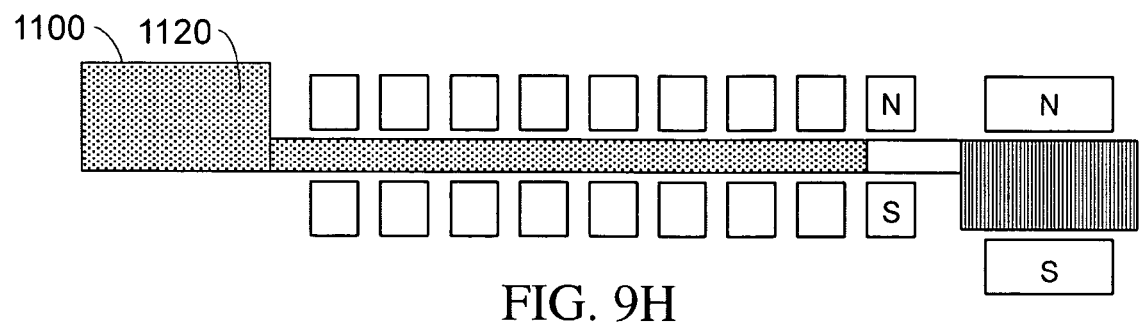

FIGS. 9E-9H illustrate an embodiment whereby the ferrofluid is transported through the gas-sampling device without employing a piston in source chamber 1100. The ferrofluid is transported from source chamber 1100, through channel 1130, and into collection chamber 1150 by alternately switching on and off the dipoles arranged along channel 1130. A suitable sequence of switching on and off those dipoles is illustrated in FIGS. 9E-9G. In FIG. 9E every other dipole is switched on, thereby drawing the ferrofluid out of source chamber 1100 and into channel 1130. A dipole is switched off when the ferrofluid reaches that dipole in the channel 1130. In this manner, and as illustrated in FIG. 9H, channel 1130 is filled with the ferrofluid in preparation switching on all the dipoles, thereby creating the magnetic field-induced structures suitable for sampling a gas.

Figure 10A:
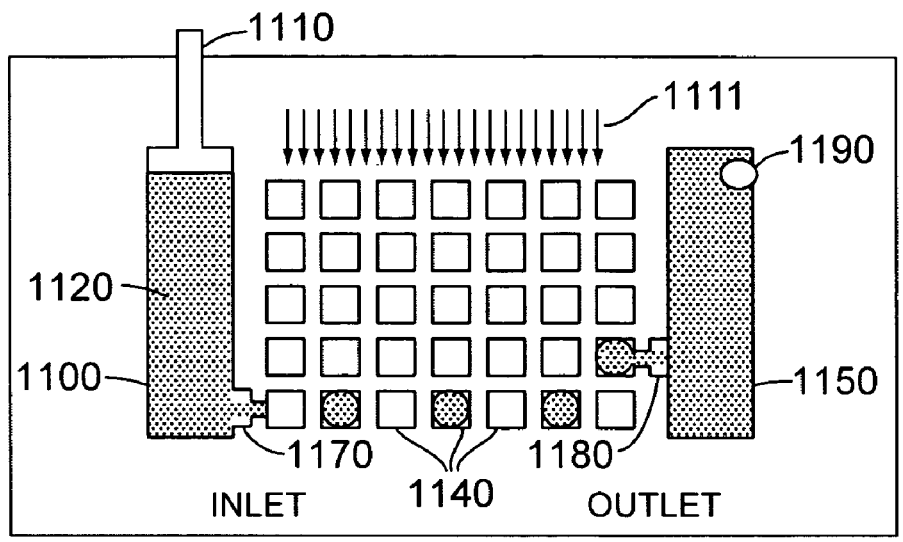

In various embodiments, there is also provided a "two-dimensional" sampling device, illustrated in FIG. 10A. The source chamber 1100 holds ferrofluid 1120 and houses optional piston 1110. Dipoles 1140 are arranged in a two-dimensional array between source chamber 1100 and collection chamber 1150, and the opposite poles are embedded in opposing substrates. The opposing substrates form a cavity through which a fluid to be sampled, such as a gas, flows (the direction of which is identified by arrows 1111). In various embodiments, inlet 1170 and outlet 1180 are each associated with a dipole. In this manner the dipole, together with a "plug" of ferrofluid, acts as a valve; for example, when the dipole associated with inlet 1170 is switched on and a magnetic field is generated, the volume within the ferrofluid inlet will solidify into a magnetic field-induced structures and prevent ferrofluid from flowing from the source chamber.

Figure 10B:
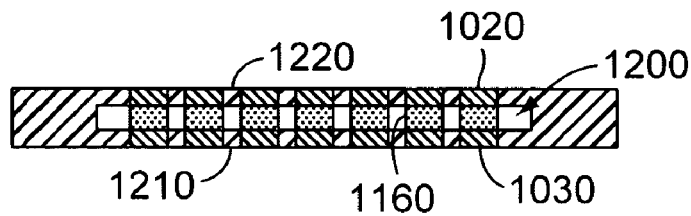

FIG. 10B illustrates a side view of the two-dimensional sampling device according to various embodiments, where a gas is permitted to flow through cavity 1200. Opposing poles 1020 and 1030 of dipoles are electrically connected to a power source, and are embedded in opposing substrates 1210 and 1220. When ferrofluid 1120 is present in cavity 1200 and the dipoles are switched on, field-induced structures 1160 of ferrofluid 1120 are formed at the gap between opposing poles 1020 and 1030.

Figure 10C:
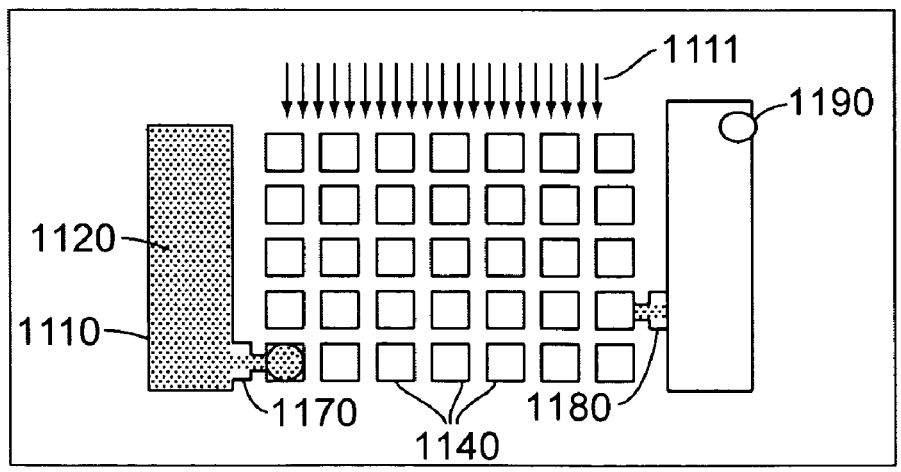
Figure 10D:
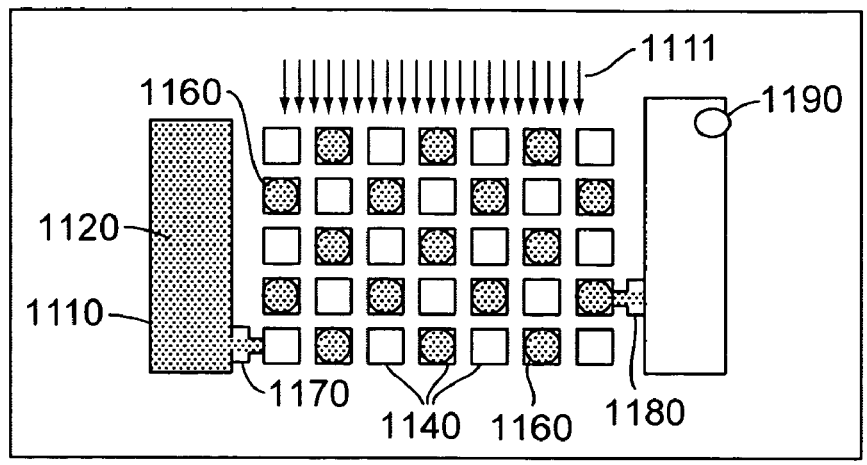
Figure 10E:
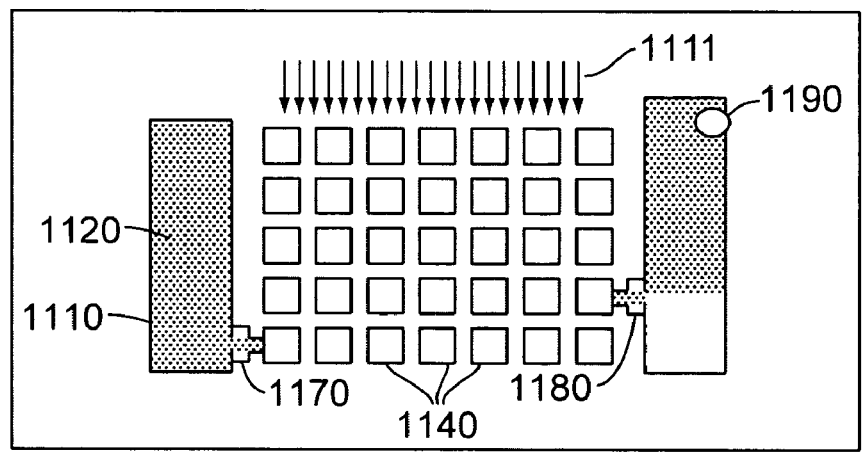

In various embodiments, the operation of the sampling device is illustrated with reference to FIG. 10C. The ferrofluid is permitted to flow from source chamber 1100 by switching off dipole 1170. Dipoles 1140 are arranged in array between the source chamber 1100 and the collection chamber 1150. By alternately switching on and off individual dipoles, the ferrofluid may be patterned (FIG. 10D) as ferrofluidic structures 1160 in the cavity between the two substrates. Gas is permitted to flow through the cavity and contact the magnetic field-induced structures. Due to the large surface-to-area ratios and the contact area between the solid and gas phase, the ability of the ferrofluidic structures to capture gas constituents is high. After a period of time, and as illustrated in FIG. 10E, the ferrofluid may be transported to the collection chamber 1150 by alternating current to dipoles 1140 and the dipole associated with outlet 1180. As the ferrofluid is collected in the chamber, it may be analyzed via sample collector 1190 for the presence and/or concentration of constituents obtained from the gas.

Figure 11:
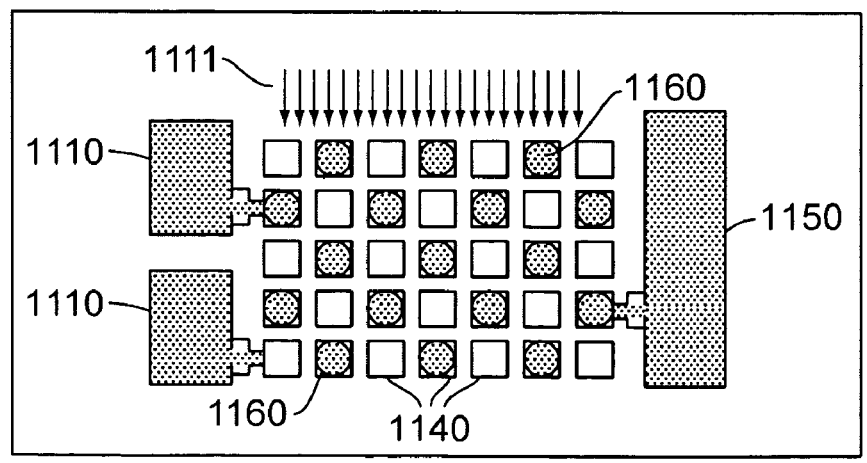

FIG. 11 illustrates another embodiment of the present disclosure. Two source chambers 1110 are fluidly connected to cavity 1200. This enables the device to operate with two types of liquids. In various embodiments, more than two source chambers might be used. There are a number of reasons why it might be desirable to use more than one type of liquid. For example, two ferrofluidic scrubbing liquids might be used because each has an affinity for different types of constituents. For example, an aqueous ferrofluidic system may be used to collect particles and/or water-soluble VOCs, whereas a non-aqueous ferrofluidic system may be employed to collect water-insoluble VOCs.

In various embodiments, it may be desirable to provide a scrubbing liquid in one source chamber and a reagent in a separate source chamber. The reagent may be employed as, e.g., a binding agent capable of binding to a substance of interest in the gas. The bound reagent is then driven into the collection chamber 1150 and subjected to an assay to determine, e.g., the presence and concentration of a substance of interest in the gas. In various embodiments a sampling device contains two source chambers each containing a reagent. In various embodiments, the reagents themselves function as scrubbing liquids. Once the reagents are driven into the collection chamber, they may be analyzed to determine the presence and concentration of a substance, or substances, of interest. In various embodiments, all of the liquids employed in the gas-sampling device exhibit certain behaviors, such as movement, in the presence of a magnetic field.

Figure 12:
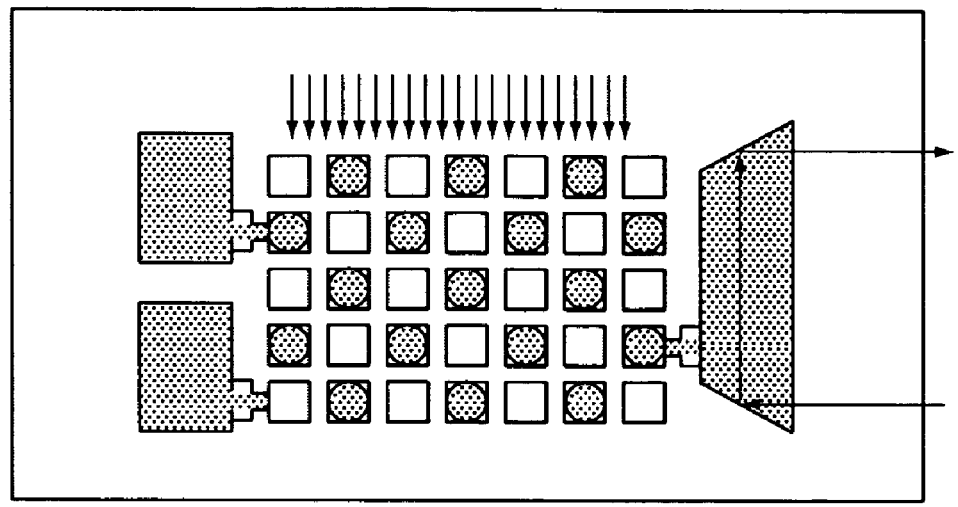

As shown in FIG. 12, a detection element comprising a mirror can be incorporated into the device. In this embodiment, the collection chamber contains a mirror on the internal chamber wall nearest surface 1115. At least a portion of the opposing wall may be transparent to allow light transmission. Light is introduced into the chamber and reflected from the mirror. Absorbance can be measured to determine, e.g., the concentration of a particular analyte in the collected liquid.

Figure 13:
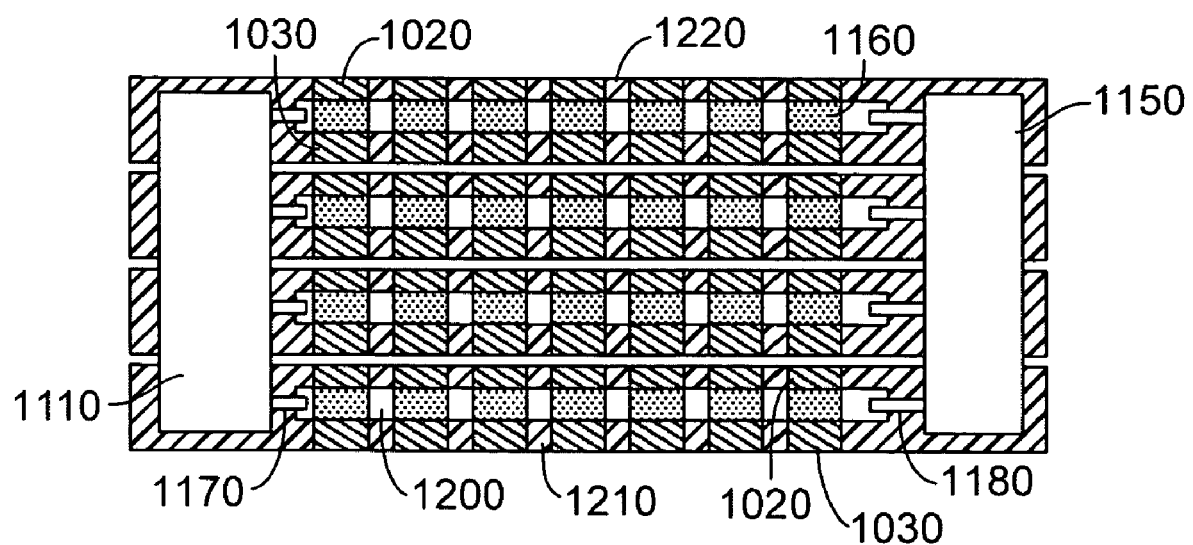

In various embodiments, multiple sampling devices can be combined into a single device. For example, the devices can be arranged as illustrated in FIG. 13. Four sampling devices are fluidly connected to a common source chamber and a common collection chamber. This arrangement may allow for an increased gas flow rate. In addition, the arrangement may allow for greater capture efficiency of at least one of aerosols, particles, and gaseous constituents.

In various embodiments, the sampling devices disclosed herein may operate, at least in part, by optical activation. In such an embodiment, a photoconductive material is electrically connected to both a power source and the magnetizable material making up the magnetic dipoles used in the devices disclosed herein. In various embodiments, the photoconductive material is disposed between a lead from the power source and the iron material. The photoconductive material is activatable by directed light to provide an electric current to the iron material, thereby generating a magnetic field.

In various embodiments, the photoconductive material used in the devices disclosed herein corresponds to a material with a dark conductivity ranging from $10^{-5}$ to $10^{-12}$ $\Omega^{-1} \cdot cm^{-1}$. The photoconductive material exhibits relatively low conductivity when dark, and relatively high conductivity when illuminated by a light source. In various embodiments, an example of a suitable photoconductive material is amorphous silicon, which has a dark conductivity of approximately $10^{-8}$ $\Omega^{-1} \cdot cm^{-1}$. In various embodiments, light with a wavelength ranging from 400 nm to 1100 nm is used to illuminate at least portions of the amorphous silicon. The light intensity for activating the sampling device can be low. For example, a light intensity that may be suitable for switching amorphous silicon is 65 mW/cm². The layer of photoconductive material permits optical control of an electrical current to a device, such as an iron bar. The photoconductive materials is configured with the iron bar so as to ensure that electrical current flows in the direction necessary to produce a magnetic field suitable for controlling a ferrofluid. Optical activation of EW and EWOD devices is further discussed in U.S. Pat. No. 6,958,132 to Chiou et al., the disclosure of which is incorporated herein by reference in its entirety.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, e.g., 1 to 5.

It is noted that, as used in this specification and the appended claims, the singular forms "a," "an," and "the," include plural referents unless expressly and unequivocally limited to one referent. Thus, for example, reference to "a charged species" includes two or more different charged species. As used herein, the term "include" and its grammatical variants are intended to be non-limiting, such that recitation of items in a list is not to the exclusion of other like items that can be substituted or added to the listed items.

It will be apparent to those skilled in the art that various modifications and variations can be made to various embodiments described herein without departing from the spirit or scope of the present teachings. Thus, it is intended that the various embodiments described herein cover other modifications and variations within the scope of the appended claims and their equivalents.

What is claimed is:

1. A method for sampling a fluid, the method comprising:
providing a sampling fluid in a directional stream;
positioning a scrubbing liquid in a pattern to intercept the sampling fluid;
contacting the sampling fluid with the scrubbing liquid to remove at least one constituent from the sampling fluid;
collecting the scrubbing liquid to collect the constituent; and
analyzing the scrubbing liquid for the presence of the constituent,
- wherein the scrubbing liquid is positioned in the pattern by electrical control.

2. The method of claim 1, wherein the sampling fluid is a gas.

3. The method of claim 2, wherein the gas is air.

4. The method of claim 1, wherein the pattern comprises of individually controllable droplets.

5. The method of claim 4, wherein the sampling fluid is a gas, and wherein the gas is air or human respiration.

6. The method of claim 4, wherein the droplets are controlled by electrowetting.

7. The method of claim 6, wherein the droplets are controlled by electrowetting on a dielectric.

8. The method of claim 7, wherein the electrowetting on a dielectric is optically activated.

9. The method of claim 7, further comprising:
- providing a gas sampling device, wherein the device comprises:
  - a first surface;
  - a second surface, parallel and proximate to the first surface;
  - a volume at least partially defined by said first and second surfaces;
  - a source chamber suitable for containing a liquid, said source chamber being fluidly connected to said volume;
  - a collection chamber suitable for containing a liquid, said collection chamber being fluidly connected to said volume; and
  - a passage allowing a flow of gas through said volume; and
- moving liquid droplets from the source chamber to the collection chamber.

10. The method of claim 9, wherein analyzing comprises providing an analytical device for performing at least one of colorimetric, fluorescent, chemiluminescent, and chromatographic analysis.

11. The method of claim 9, further comprising:
- providing a plurality of air sampling devices, wherein the devices are positioned in a parallel stack or in series.

12. The method of claim 9, wherein the collection chamber is fluidly connected to a mass spectrometer, a liquid chromatograph, or a gas chromatograph.

13. The method of claim 1, wherein the pattern comprises of individually controllable structures.

14. The method of claim 13, wherein the scrubbing liquid comprises ferrofluids.

15. The method of claim 14, wherein the sampling fluid is a gas, and wherein the gas is air or human respiration.

16. The method of claim 14, further comprising:
providing a gas sampling device, wherein the device comprises:
- a first surface;
- a second surface, parallel and proximate to the first surface;
- a cavity at least partially defined by said first and second surfaces;
- a plurality of magnetizable structures, each of which is shaped so as to provide two ends, wherein each end functions as one pole of a dipole when the ferrofluid is magnetized, and wherein the ends oppose each other across said cavity;
- a power source configured to provide an electric current to the plurality of magnetizable structures in a manner that generates a magnetic field across said cavity; and
- a passage fluidly coupled with said cavity.

17. The method of claim 16, further comprising optically activating the ferrofluid structures.

18. The method of claim 16, wherein the ferrofluid is hydrophilic or hydrophobic.

19. The method of claim 16, wherein analyzing comprises providing an analytical device for performing at least one of colorimetric, fluorescent, chemiluminescent, and chromatographic analysis.

20. The method of claim 16, wherein the collection chamber is fluidly connected to a mass spectrometer, a liquid chromatograph, or a gas chromatograph.

21. A method for sampling gases, the method comprising:
providing a gas in a directional stream;
positioning a scrubbing liquid in a pattern droplets to intercept the gas;
contacting the gas with the scrubbing liquid to remove at least one constituent from the gas;
collecting the scrubbing liquid to collect the constituent; and
analyzing the scrubbing liquid for the presence of the constituent,
wherein the scrubbing liquid is positioned in the pattern of droplets by electrowetting on a dielectric.

22. A method for sampling gases, the method comprising:
providing a gas in a directional stream;
positioning a scrubbing liquid in a pattern of ferrofluid structures to intercept the gas;
contacting the gas with the scrubbing liquid to remove at least one constituent from the gas;
collecting the scrubbing liquid to collect the constituent; and
analyzing the scrubbing liquid for the presence of the constituent,
wherein the scrubbing liquid is positioned in the pattern of ferrofluid structures by applying a magnetic field to the ferrofluid.

* * * * *